United States Patent
Kawrykow et al.

(10) Patent No.: US 9,966,160 B2
(45) Date of Patent: May 8, 2018

(54) RADIATION BEAM COLLIMATING SYSTEMS AND METHODS

(71) Applicant: ViewRay Techonologies, Inc., Oakwood Village, OH (US)

(72) Inventors: Iwan Kawrykow, Sofia (BG); James F. Dempsey, Atherton, CA (US); Gopinath Kuduvalli, Cupertino, CA (US); Gerald E. Fought, Columbia Station, OH (US); Amit Sharma, Mayfield Heights, OH (US)

(73) Assignee: ViewRay Technologies, Inc., Oakwood Village, OH (US)

( * ) Notice: Subject to any disclaimer, the term of this patent is extended or adjusted under 35 U.S.C. 154(b) by 0 days. days.

(21) Appl. No.: 15/359,503

(22) Filed: Nov. 22, 2016

(65) Prior Publication Data

US 2017/0148536 A1    May 25, 2017

Related U.S. Application Data

(60) Provisional application No. 62/259,570, filed on Nov. 24, 2015.

(51) Int. Cl.
*G21K 1/04* (2006.01)
*G21K 1/02* (2006.01)
*A61N 5/10* (2006.01)

(52) U.S. Cl.
CPC ........... *G21K 1/046* (2013.01); *A61N 5/1045* (2013.01); *A61N 5/1077* (2013.01)

(58) Field of Classification Search
USPC ...... 250/505.1, 519.1, 526; 378/64, 65, 147, 378/150, 152, 155, 157
See application file for complete search history.

(56) References Cited

U.S. PATENT DOCUMENTS

| 4,694,837 A | 9/1987 | Blakeley et al. |
| 4,987,309 A * | 1/1991 | Klasen ................ A61N 5/1042 250/492.1 |

(Continued)

FOREIGN PATENT DOCUMENTS

| FR | 2839894 A1 | 11/2003 |
| JP | 2002186676 A | 7/2001 |

(Continued)

OTHER PUBLICATIONS

Balter, James M., et al. "Accuracy of a Wireless Localization System for Radiotherapy" *Int. J. Radiation Oncology Biol. Phys.*, vol. 61, No. 3. pp. 933-937. 2005. Elsevier Inc., USA. Accepted for publication Nov. 1, 2004.

(Continued)

*Primary Examiner* — Bernard Souw
(74) *Attorney, Agent, or Firm* — Pillsbury Winthrop Shaw Pittman LLP

(57) ABSTRACT

A collimating system for collimating a radiation beam having a first multileaf collimator and a second multileaf collimator configured such that the radiation beam will pass through the first multileaf collimator before passing through the second multileaf collimator, and pass through the second multileaf collimator before hitting its target. The leaves of the first multileaf collimator and the leaves of the second multileaf collimator may be configured to move independently of one another.

24 Claims, 9 Drawing Sheets

(56) References Cited

U.S. PATENT DOCUMENTS

| | | |
|---|---|---|
| 5,216,255 A | 6/1993 | Weidlich |
| 5,317,616 A | 5/1994 | Swerdloff et al. |
| 5,332,908 A | 7/1994 | Weidlich |
| 5,351,280 A * | 9/1994 | Swerdloff ............ A61N 5/1042 378/150 |
| 5,373,844 A | 12/1994 | Smith et al. |
| 5,442,675 A | 8/1995 | Swerdloff et al. |
| 5,458,125 A | 10/1995 | Schweikard |
| 5,513,238 A | 4/1996 | Leber et al. |
| 5,537,452 A | 7/1996 | Shepherd et al. |
| 5,538,494 A | 7/1996 | Matsuda |
| 5,555,283 A | 9/1996 | Shiu et al. |
| 5,596,619 A * | 1/1997 | Carol ..................... A61N 5/01 378/150 |
| 5,602,892 A | 2/1997 | Llacer |
| 5,724,400 A | 3/1998 | Swerdloff et al. |
| 5,734,384 A | 3/1998 | Yanof et al. |
| 5,740,225 A | 4/1998 | Nabatame |
| 5,748,700 A | 5/1998 | Shepherd et al. |
| 5,751,781 A | 5/1998 | Brown et al. |
| 5,757,881 A * | 5/1998 | Hughes ................. A61N 5/1042 250/505.1 |
| 5,802,136 A | 9/1998 | Carol |
| 5,815,547 A | 9/1998 | Shepherd et al. |
| 5,894,503 A | 4/1999 | Shepherd et al. |
| 6,038,283 A | 3/2000 | Carol et al. |
| 6,052,430 A | 4/2000 | Siochi et al. |
| 6,104,779 A | 8/2000 | Shepherd et al. |
| 6,112,112 A | 8/2000 | Gilhuijs et al. |
| 6,144,875 A | 11/2000 | Schweikard et al. |
| 6,175,761 B1 | 1/2001 | Frandsen et al. |
| 6,198,957 B1 | 3/2001 | Green |
| 6,223,067 B1 | 4/2001 | Vilsmeier et al. |
| 6,240,162 B1 | 5/2001 | Hernandez-Guerra et al. |
| 6,314,159 B1 | 11/2001 | Siochi |
| 6,330,300 B1 | 12/2001 | Siochi |
| 6,349,129 B1 | 2/2002 | Siochi |
| 6,366,798 B2 | 4/2002 | Green |
| 6,381,486 B1 | 4/2002 | Mistretta et al. |
| 6,385,286 B1 | 5/2002 | Fitchard et al. |
| 6,385,477 B1 | 5/2002 | Werner et al. |
| 6,393,096 B1 | 5/2002 | Carol et al. |
| 6,411,675 B1 | 6/2002 | Llacer |
| 6,414,487 B1 | 7/2002 | Anand et al. |
| 6,422,748 B1 | 7/2002 | Shepherd et al. |
| 6,424,856 B1 | 7/2002 | Vilsmeier et al. |
| 6,459,769 B1 * | 10/2002 | Cosman ................ A61N 5/1042 250/505.1 |
| 6,466,813 B1 | 10/2002 | Shukla et al. |
| 6,487,435 B2 | 11/2002 | Mistretta et al. |
| 6,504,899 B2 | 1/2003 | Pugachev et al. |
| 6,512,813 B1 | 1/2003 | Krispel et al. |
| 6,516,046 B1 | 2/2003 | Frohlich et al. |
| 6,526,123 B2 | 2/2003 | Ein-Gal |
| 6,527,443 B1 | 3/2003 | Vilsmeier et al. |
| 6,542,767 B2 | 4/2003 | McNichols et al. |
| 6,546,073 B1 | 4/2003 | Lee |
| 6,560,311 B1 | 5/2003 | Shepard et al. |
| 6,584,174 B2 | 6/2003 | Schubert et al. |
| 6,594,516 B1 | 7/2003 | Steckner et al. |
| 6,600,810 B1 | 7/2003 | Hughes |
| 6,609,022 B2 | 8/2003 | Vilsmeier et al. |
| 6,611,700 B1 | 8/2003 | Vilsmeier et al. |
| 6,618,467 B1 | 9/2003 | Ruchala et al. |
| 6,661,870 B2 | 12/2003 | Kapatoes et al. |
| 6,708,054 B2 | 3/2004 | Shukla et al. |
| 6,719,683 B2 | 4/2004 | Frohlich |
| 6,724,922 B1 | 4/2004 | Vilsmeier |
| 6,728,336 B2 | 4/2004 | Bortfeld et al. |
| 6,731,970 B2 | 5/2004 | Schlossbauer et al. |
| 6,735,277 B2 | 5/2004 | McNutt et al. |
| 6,757,355 B1 | 6/2004 | Siochi |
| 6,772,002 B2 | 8/2004 | Schmidt et al. |
| 6,778,850 B1 | 8/2004 | Adler et al. |
| 6,792,074 B2 | 9/2004 | Erbel et al. |
| 6,853,704 B2 | 2/2005 | Collins et al. |
| 6,859,660 B2 | 2/2005 | Vilsmeier |
| 6,862,469 B2 | 3/2005 | Bucholz et al. |
| 6,865,253 B2 | 3/2005 | Blumhofer et al. |
| 6,865,411 B2 | 3/2005 | Erbel et al. |
| 6,879,714 B2 | 4/2005 | Hutter |
| 6,885,886 B2 | 4/2005 | Bauch et al. |
| 6,898,456 B2 | 5/2005 | Erbel |
| 6,915,005 B1 | 7/2005 | Ruchala et al. |
| 6,937,696 B1 | 8/2005 | Mostafavi |
| 6,947,582 B1 | 9/2005 | Vilsmeier et al. |
| 6,965,847 B2 | 11/2005 | Wessol et al. |
| 6,980,679 B2 | 12/2005 | Jeung et al. |
| 6,999,555 B2 | 2/2006 | Morf |
| 7,046,762 B2 | 5/2006 | Lee |
| 7,046,765 B2 | 5/2006 | Wong et al. |
| 7,046,831 B2 | 5/2006 | Ruchala et al. |
| 7,050,845 B2 | 5/2006 | Vilsmeier |
| 7,095,823 B2 | 8/2006 | Topolnjak et al. |
| 7,096,055 B1 | 8/2006 | Schweikard |
| 7,123,758 B2 | 10/2006 | Jeung et al. |
| 7,130,372 B2 | 10/2006 | Kusch et al. |
| 7,154,991 B2 | 12/2006 | Earnst et al. |
| 7,166,852 B2 | 1/2007 | Saracen et al. |
| 7,171,257 B2 | 1/2007 | Thomson |
| 7,180,366 B2 | 2/2007 | Roos et al. |
| 7,191,100 B2 | 3/2007 | Mostafavi |
| 7,204,640 B2 | 4/2007 | Fu et al. |
| 7,221,733 B1 | 5/2007 | Takai et al. |
| 7,227,925 B1 | 6/2007 | Mansfield et al. |
| 7,231,075 B2 | 6/2007 | Raghavan et al. |
| 7,231,076 B2 | 6/2007 | Fu et al. |
| 7,260,426 B2 | 8/2007 | Schweikard et al. |
| 7,266,175 B1 | 9/2007 | Romesberg |
| 7,266,176 B2 | 9/2007 | Allison et al. |
| 7,289,599 B2 | 10/2007 | Seppi et al. |
| 7,298,819 B2 | 11/2007 | Dooley et al. |
| 7,302,038 B2 | 11/2007 | Mackie et al. |
| 7,315,636 B2 | 1/2008 | Kuduvalli |
| 7,318,805 B2 | 1/2008 | Schweikard et al. |
| 7,324,626 B2 | 1/2008 | Vilsmeier et al. |
| 7,327,865 B2 | 2/2008 | Fu et al. |
| 7,366,278 B2 | 4/2008 | Fu et al. |
| 7,403,638 B2 | 7/2008 | Jeung et al. |
| 7,412,029 B2 | 8/2008 | Myles |
| 7,415,095 B2 | 8/2008 | Wofford et al. |
| 7,423,273 B2 | 9/2008 | Clayton et al. |
| 7,426,318 B2 | 9/2008 | Fu et al. |
| 7,444,178 B2 | 10/2008 | Goldbach |
| 7,463,823 B2 | 12/2008 | Birkenbach et al. |
| 7,471,813 B2 | 12/2008 | Ulmer et al. |
| 7,477,776 B2 | 1/2009 | Lachner et al. |
| 7,480,399 B2 | 1/2009 | Fu et al. |
| 7,505,037 B2 | 3/2009 | Wang |
| 7,505,617 B2 | 3/2009 | Fu et al. |
| 7,522,779 B2 | 4/2009 | Fu et al. |
| 7,558,617 B2 | 7/2009 | Vilsmeier |
| 7,570,987 B2 | 8/2009 | Raabe et al. |
| 7,577,474 B2 | 8/2009 | Vilsmeier |
| 7,589,326 B2 | 9/2009 | Mollov et al. |
| 7,634,122 B2 | 12/2009 | Bertram et al. |
| 7,636,417 B2 | 12/2009 | Bjorkholm |
| 7,638,752 B2 | 12/2009 | Partain et al. |
| 7,657,304 B2 | 2/2010 | Mansfield et al. |
| 7,688,998 B2 | 3/2010 | Tuma et al. |
| 7,907,987 B2 | 3/2011 | Dempsey |
| 8,190,233 B2 | 5/2012 | Dempsey |
| 8,637,841 B2 * | 1/2014 | Prince .................. A61N 5/1045 250/492.1 |
| 9,082,520 B2 * | 7/2015 | Prince .................. A61N 5/1045 |
| 2001/0049475 A1 | 12/2001 | Bucholz et al. |
| 2002/0046010 A1 | 4/2002 | Wessol et al. |
| 2002/0091315 A1 | 7/2002 | Spetz |
| 2002/0131556 A1 * | 9/2002 | Steinberg ............. A61N 5/1042 378/152 |
| 2002/0150207 A1 | 10/2002 | Kapatoes et al. |
| 2003/0155530 A1 | 8/2003 | Adnani et al. |
| 2003/0181804 A1 | 9/2003 | Gagnon et al. |
| 2003/0219098 A1 | 11/2003 | McNutt et al. |

(56) References Cited

U.S. PATENT DOCUMENTS

| | | | |
|---|---|---|---|
| 2004/0254448 | A1 | 12/2004 | Amies et al. |
| 2004/0254773 | A1 | 12/2004 | Zhang et al. |
| 2005/0053267 | A1 | 3/2005 | Mostafavi |
| 2005/0054916 | A1 | 3/2005 | Mostafavi |
| 2005/0201516 | A1 | 9/2005 | Ruchala et al. |
| 2006/0058636 | A1 | 3/2006 | Wemple et al. |
| 2006/0074292 | A1 | 4/2006 | Thomson et al. |
| 2007/0197908 | A1 | 8/2007 | Ruchala et al. |
| 2007/0244386 | A1 | 10/2007 | Steckner et al. |
| 2009/0129545 | A1 | 5/2009 | Adler et al. |
| 2012/0043482 | A1* | 2/2012 | Prince ............... G21K 1/046 250/505.1 |
| 2014/0112453 | A1* | 4/2014 | Prince ............... G21K 1/046 378/152 |
| 2015/0273239 | A1* | 10/2015 | Hsu ................. A61N 5/1045 378/150 |

FOREIGN PATENT DOCUMENTS

| | | |
|---|---|---|
| JP | 2002522129 A | 7/2002 |
| JP | 2007526036 A | 9/2007 |
| WO | WO-99/32189 A1 | 7/1999 |
| WO | WO-02/072190 A2 | 9/2002 |
| WO | WO-03/008986 A2 | 1/2003 |
| WO | WO-2004/024235 A1 | 3/2004 |
| WO | WO-2006/097274 A1 | 9/2006 |

OTHER PUBLICATIONS

Bernier, Jacques et al. "Radiation oncology: a century of achievements" *Nature Reviews | Cancer.* vol. 4, Sep. 2004. pp. 737-747.

Buchanan, Roger. "Cobalt on the way out" British Medical Journal, vol. 292, Feb. 1, 1986. p. 290.

Chng, N. et al. "Development of inverse planning and limited angle CT reconstruction for cobalt-60 tomotherapy" *Proceedings of 51st Annual Meeting of Canadian Organization of Medical Physicists and the Canadian College of Physicists in Medicine,* 2005, McMaster University, Hamilton Ontario. Medical Physics, 2005, pp. 2426.

De Poorter, John et al. "Noninvasive MRI Thermometry with the Proton Resonance Frequency (PRF) Method: In Vivo Results in Human Muscle." *MRM* 33 (1995). pp. 74-81.

Goitein, Michael. "Organ and Tumor Motion: An Overview." *Seminars in Radiation Oncology.* vol. 14, No. 1 Jan. 2004: pp. 2-9.

Goldberg, S., Nahum, Gazelle, G. Scott and Mueller, Peter R. "Thermal Ablation Therapy for Focal Malignancy: A Unified Approach to Underlying Principles, Techniques, and Diagnostic Imaging Guidance." *AJR*:174. Feb. 2000. pp. 323-331.

Hajdok, George. "An Investigation of Megavoltage Computed Tomography Using a Radioactive Cobalt-60 Gamma Ray Source for Radiation Therapy Treatment Verification." Thesis. May 2002. 150 pages.

Jaffray, David A., et al. "Flat-Panel Cone-Beam Computed Tomography for Image-Guided Radiation Therapy." *Int. J. Radiation Oncology Biol. Phys.*, vol. 53, No. 5, 2002. pp. 1337-1349. Elsevier Science Inc., USA.

Jursinic, Paul et al. "Characteristics of secondary electrons produced by 6, 10 and 24 MV x-ray beams." *Phys. Med. Biol.* 41 (1996) pp. 1499-1509, United Kingdom.

Khan, Faiz M., "The Physics of Radiation Therapy (second edition)." Lippincott Williams & Wilkins. 1985. pp. 323-332.

Lagendijk J. J. et al. "MRI guided radiotherapy: A MRI based linear accelerator." Radiotherapy & Oncology. vol. 56, No. Supplement 1. Sep. 2000. (Sep. 2000):S60-S61. *19th Annual Meeting of the European Society for Therapeutic Radiology and Oncology.* Istanbul, Turkey; Sep. 21, 2000.

Langen, K.M. et al. "Organ Motion and its Management." *Int. J. Radiation Oncology Biol. Phys.*, vol. 50, No. 1, pp. 265-278. 2001. Elsevier Science Inc., USA.

Liang, J. and Yan, D. "Reducing uncertainties in volumetric image based deformable organ registration." Med. Phys. 30(8) Aug. 2003. pp. 2116-2122.

Lurie, D.J., PhD. "Free radical imaging" *The British Journal of Radiology.* 74 (2001). pp. 782-784.

Raaijmakers, A.J.E. et al. "Integrating a MRI scanner with a 6 MV radiotherapy accelerator: dose increase at tissue-air interfaces in a lateral magnetic field due to returning electrons." *Phys. Med. Biol.* 50 (2005) pp. 1363-1376.

Schreiner, L. John, et al. "The Potential for Image Guided Radiation Therapy with Cobalt-60 Tomotherapy.", *MICCAI* 2003. LNCS 2879, pp. 449-456, 2003.

Schreiner, L. John, et al. "The role of Cobalt-60 in modern radiation therapy: Dose delivery and image guidance." *Journal of Medical Physics.* vol. 34, No. 3. 2009. pp. 133-136.

Sempau, Josep et al. "DPM, a fast, accurate Monte Carlo code optimized for photon and electron radiotherapy treatment planning dose calculations." *Phys. Med. Biol.* 45 (2000) pp. 2263-2291. Printed in the UK.

Sherouse, George W. et al. "Virtual Simulation in the Clinical Setting: Some Practical Considerations." *Int. J. Radiation Oncology Biol. Phys.* 1990. vol. 19. No. 4. pp. 1059-1065. Pergamon Press, USA.

Tamada and Kose. "Two-Dimensional Compressed Sensing Using the Cross-sampling Approach for Low-Field MRI Systems." IEEE Transactions on Medical Imaging. vol. 33, No. 9. Sep. 2014. Pages 1905-1912.

Tokuda, Junichi et al. "Motion Tracking in MR-Guided Liver Therapy by Using Navigator Echoes and Projection Profile Matching." *Academic Radiology.* vol. 11, No. 1, Jan. 2004. pp. 111-120.

Warrington, Jim et al. "Cobalt 60 Teletherapy for Cancer: A Revived Treatment Modality for the 21st Century." *The Institution of Electrical Engineers.* 2002, pp. 19-1-19/19.

Wazer, David E. et al. "Principles and Practice of Radiation Oncology (fifth edition).", Wolters Kluwer/Lippincott Williams & Wilkins. 2008. 2 pages.

Webb, Steve. "Historical Perspective on IMRT." *Institute of Cancer Research and Royal Marsden NHS Trust.* 2002.

Webb, S. "The physical basis of IMRT and inverse planning." *The British Journal of Radiology.* 76 (2003), pp. 678-689, 2003.

* cited by examiner

RADIATION BEAM COLLIMATING SYSTEMS AND METHODS

RELATED APPLICATION

This application claims the benefit of U.S. Provisional Application No. 62/259,570, filed Nov. 24, 2015, which is hereby incorporated by reference.

BACKGROUND

The present disclosure relates to systems and methods for collimating or shaping a radiation beam. Collimators are typically made from high atomic number materials, such as tungsten, and are therefore able to attenuate a significant amount of radiation. Collimators may be used, for example, to shape a radiation beam for the purpose of providing precise medical radiation therapy.

SUMMARY

In one implementation, a collimating system collimates a radiation beam from a radiation source, the beam being directed at a target. The collimating system includes a first multileaf collimator having a number of leaves, and a second multileaf collimator having a number of leaves. The collimating system is configured such that the radiation beam will pass through the first multileaf collimator before passing through the second multileaf collimator, and pass through the second multileaf collimator before hitting the target. The leaves of the first multileaf collimator and the leaves of the second multileaf collimator are configured to move independently of one another. At least one of the first multileaf collimator and the second multileaf collimator is double focused.

In some variations one or more of the following features can optionally be included in any feasible combination.

The first multileaf collimator and the second multileaf collimator can both be double focused, configured to be slightly defocused to decrease radiation leakage through interleaf gaps, or can be configured to be defocused by approximately 1 centimeter.

The first multileaf collimator can have a focus point and the second multileaf collimator can have a focus point and the focus point of the first multileaf collimator can be different from the focus point of the second multileaf collimator. The differing focus points of the first multileaf collimator and the second multileaf collimator can improve the match of penumbra between the first multileaf collimator and the second multileaf collimator. The focus point of the first multileaf collimator can be at the effective source point and the focus point of the second multileaf collimator moved off of the effective source point. The first multileaf collimator and second multileaf collimator can further be configured to collimate a beam thinner than the widths of the leaves of the first and second multileaf collimators.

The leaves of the first multileaf collimator can have approximately the same width as the leaves of the second multileaf collimator. The leaves of the first multileaf collimator can be immediately adjacent to one another and the leaves of the second multileaf collimator can be immediately adjacent to one another.

The gaps between adjacent leaves in the first multileaf collimator and gaps between adjacent leaves in the second multileaf collimator can be minimized to reduce radiation leakage.

The leaves of both the first multileaf collimator and the second multileaf collimator can be approximately 4 mm wide.

The leaves of the first multileaf collimator and the leaves of the second multileaf collimator can be offset by approximately 50% of their width.

The thickness of the leaves of the first multileaf collimator and the thickness of the leaves of the second multileaf collimator can be approximately the same, can be each sufficient to fully attenuate the radiation beam for medical radiation therapy, or can be approximately 5.5 cm.

The mating surfaces of the leaves can be straight edged, machined to provide a tongue and groove interface, or machined to provide a step interface.

The leaves of the first and second multileaf collimators can include leaf assemblies utilizing a frame separate from an attenuating material. The frame can be made from a stainless steel alloy and the attenuating material can be a tungsten alloy.

The first multileaf collimator can have two banks and each bank includes 34 leaves and the second multileaf collimator can have two banks and each bank includes 35 leaves.

The edge of the collimating system closest to the target can be less than 60 cm from a radiation isocenter. The collimating system can optionally not include collimator jaws.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
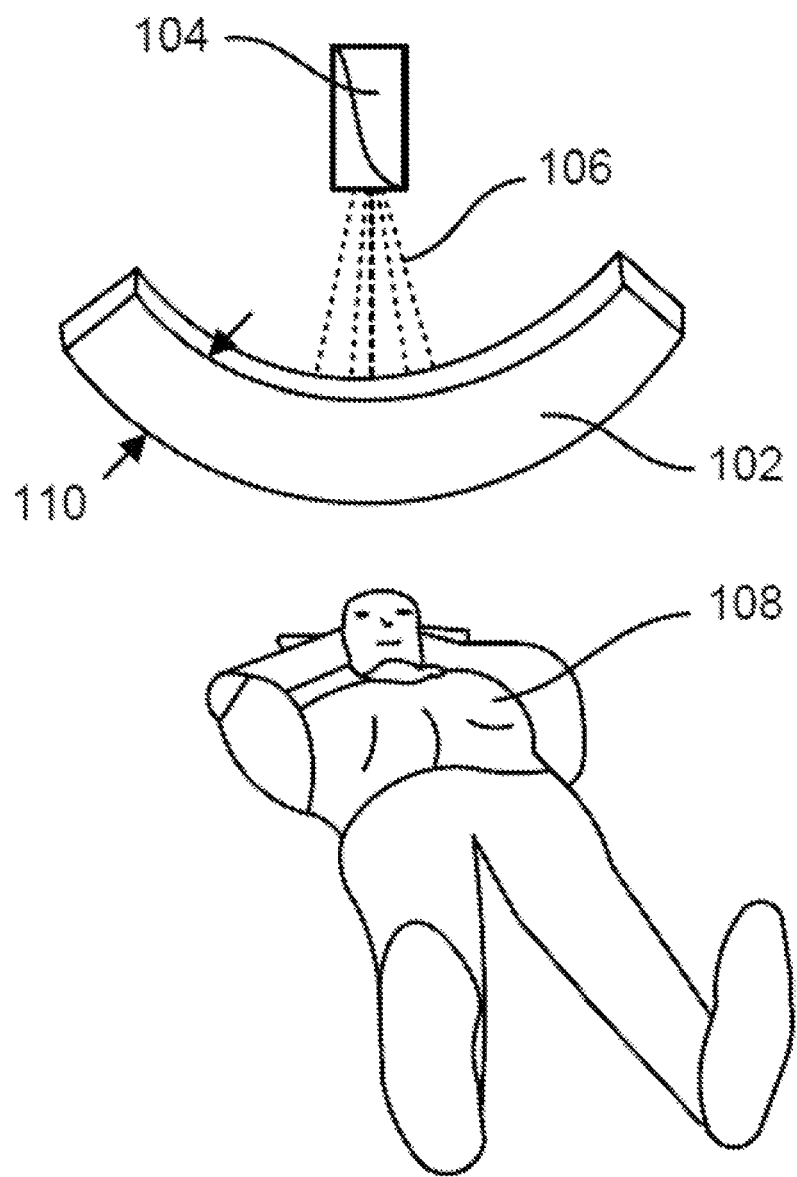
FIG. 1 is a simplified diagram illustrating an exemplary use of a collimating device with a radiation source.

An exemplary use for a collimating device/system is depicted in FIG. 1. As shown, collimating device 102 is placed in the path of a radiation beam 106 emanating from a radiation source 104. Collimating device 102 enables selective attenuation of the radiation beam 106 as it travels toward target 108. The radiation source 104 may be, for example, a radioisotope, a heavy ion accelerator, a linear accelerator for producing an electron or photon beam, or the like. While the technology of the present disclosure may be used in any field where radiation beams are utilized, an embodiment described herein depicts a medical patient as target 108.

Figure 2:
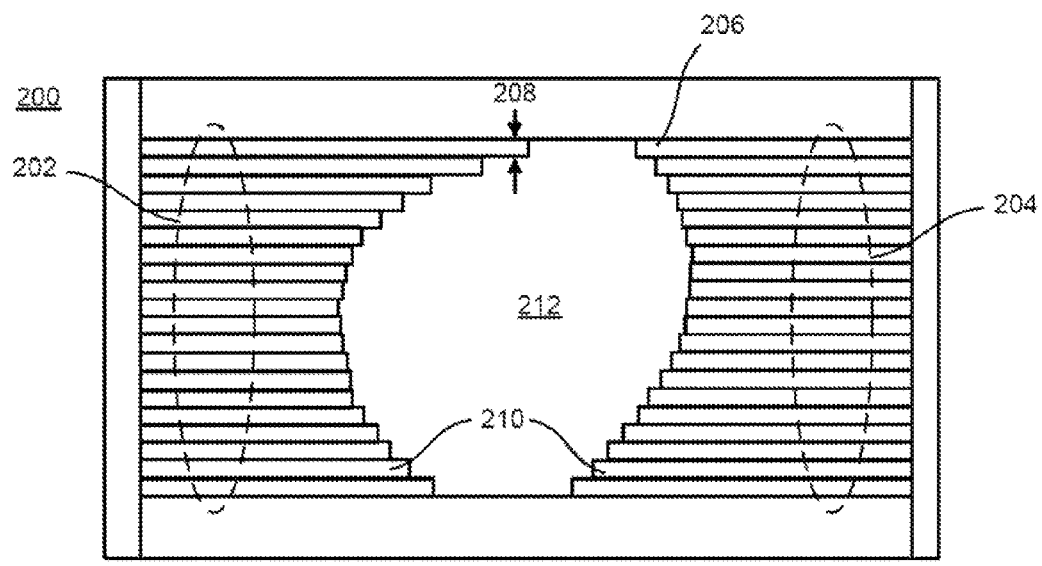
FIG. 2 is a simplified illustration of an exemplary multi-leaf collimator and the manner in which it can create an aperture.

FIG. 2 depicts a particular type of collimating device known as a Multi-Leaf Collimator (or MLC). The exemplary MLC 200 shown includes a bank of movable leaves 202 opposite a second bank of movable leaves 204. In such a device, each leaf 206 is independently adjustable in order to enable the forming of an aperture 212, which collimates the beam into the desired shape for treatment.

Each leaf in MLC 200 may be described as having a width 208 and a height 110 (height is shown in FIG. 1). The height 110 may also be described as the "thickness" of a leaf and is important in determining the amount of attenuation of beam 106 by MLC 200. The amount of attenuation is also affected by the material that the leaves of the MLC are made of and therefore high-attenuating materials are used such as tungsten, tungsten alloys, tantalum, tantalum alloys, lead, lead alloys and the like.

Figure 3:
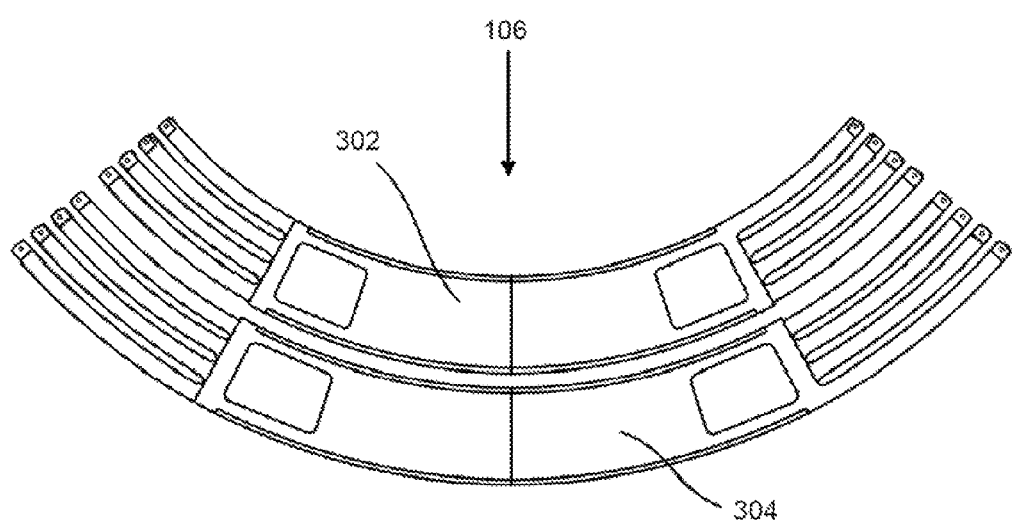
FIG. 3 is a simplified illustration of an exemplary double-stacked collimating device in accordance with certain aspects of the present disclosure.

An exemplary collimating system contemplated by the present disclosure is depicted in FIG. 3 and comprises multiple "stacked" MLCs. For example, the embodiment depicted includes a first MLC 302 and a second MLC 304. The MLCs are stacked such that their attenuation values are additive with respect to radiation beam 106. The first MLC 302 is positioned closer to radiation source 104 than second MLC 304, so that radiation beam 106 passes through first MLC 302 before passing through second MLC 304. The embodiments depicted herein show two stacked MLCs but it is contemplated that additional MLCs could be added (e.g., a stack of three) following the general teachings of the present disclosure.

While it is common for collimating devices to be placed close to radiation source 104, the present disclosure contemplates an embodiment that moves the collimating device closer to the target or patient. For example, a preferred implementation of the present disclosure moves the collimating device as close to the target as possible, without restricting the desired bore or volume to be occupied by the target/patient. In one preferred implementation, the edge of the collimating device closest to target 108 (i.e., the edge of the second MLC 304 that is farthest from radiation source 104) is less than 60 cm from isocenter, and preferably about 50 cm from isocenter. It is contemplated that such a design facilitates positioning of the collimating device during assembly and decreases beam penumbra.

Figure 4A:
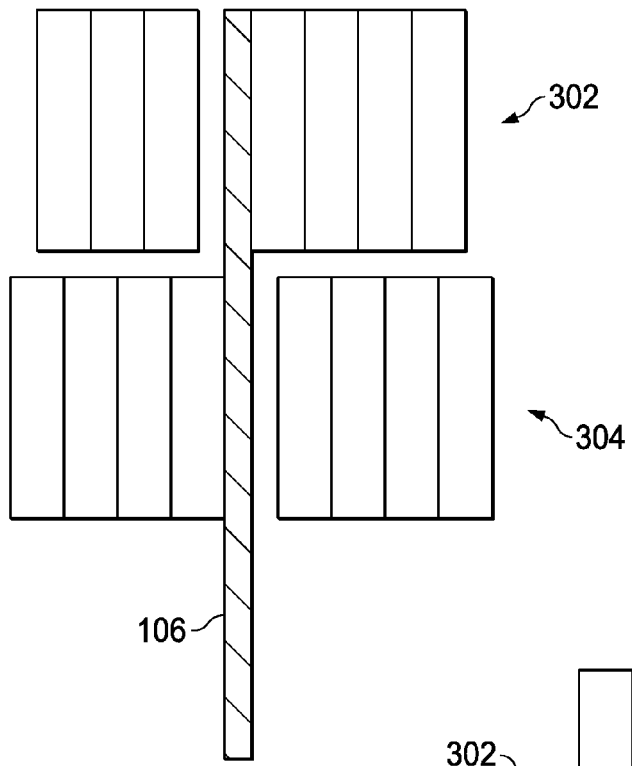
FIGS. 4A and 4B are simplified illustrations of a manner in which a double stacked collimating device may collimate a radiation beam
Figure 4B:
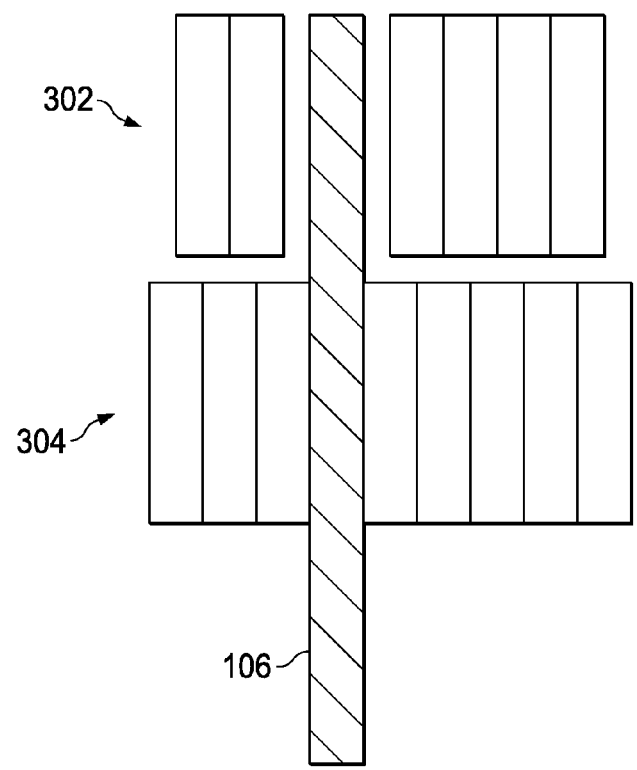

FIG. 4A and FIG. 4B are simplified illustrations of how beams may be collimated with an exemplary double-stacked MLC system. As shown in both figures, the leaves in the first MLC 302 and second MLC 304 are offset by one half the width of the leaves, or by approximately one half of the width of the leaves. The leaves in first MLC 302 and second MLC 304 can be moved independently of one another. In FIG. 4A, one leaf in first MLC 302 and one leaf in second MLC 304 can be retracted to create the smallest aperture through which beam 106 may pass (in the dimension corresponding to the width of the leaves). As a result, the leaves of the MLCs are offset in a manner to allow for collimation of a beam thinner than the widths of the leaves of each of the first and second multileaf collimators.

In one particular implementation, the width of such a beam may be 4.15 mm when the width of the leaves in both first MLC 302 and second MLC 304 are approximately 8.3 mm. FIG. 4B shows that when two leaves of one of the MLCs are retracted and an overlapping leaf in the other MLC is retracted, the second smallest aperture through which radiation beam 106 may pass is created, for example, a beam having a width of 8.3 mm.

In one implementation, the MLCs are stacked, the leaves in each MLC are approximately the same width, and the leaves in first MLC 302 are offset from the leaves in second MLC 304 by approximately one-half of their width (as shown in FIG. 4). The MLC leaves in such an implementation may be designed to be approximately twice the width of a typical MLC, while still achieving approximately the same resolution. For example, to achieve a 5 mm resolution at isocenter, a typical single MLC will require leaves approximately 2.5 mm wide, while in a double-stacked design with offset, the leaves may be approximately 5 mm wide and achieve the same resolution. Such a design may be desirable for ease of machining and to provide more material for equipment connecting to or interfacing with the leaves.

Figure 5:
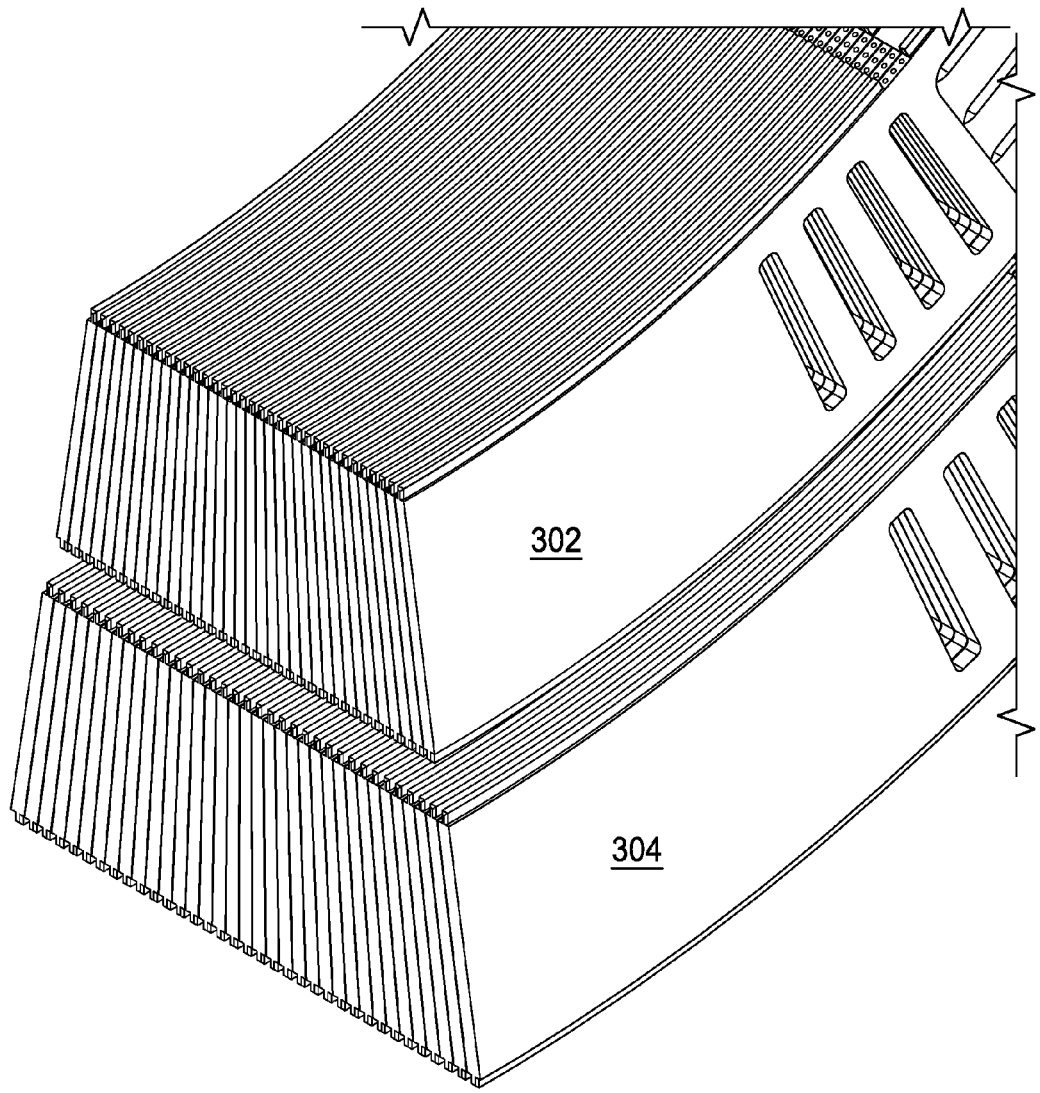
FIG. 5 is a simplified isometric illustration of an exemplary double-stacked collimating device in accordance with certain aspects of the present disclosure.

FIG. 5 is an isometric view of the exemplary collimating system of FIG. 3 showing double stacked MLCs 302 and 304. Because the exemplary collimating system includes multiple MLCs, arranged to have an additive beam attenuating affect, the leaves in each of the individual MLCs may have a decreased height, or thickness, compared to the leaves in a standard single MLC collimating system. As an example, where two MLCs are utilized, the leaves in each MLC may be approximately one half the height of the leaves in a typical single MLC made of the same material. Such may decrease the weight of individual leaves, making them easier to control and allowing for more rapid movement, which can reduce overall treatment time. Moreover, if the collimators are designed to be focused or double focused (as preferred, and described further below), the edges of the MLCs exposed to the beam will have greater attenuation and the leaves of each of the MLCs may be further decreased in height.

Given the beam collimating features shown in FIG. 4, and the importance of beam attenuation described herein, preferred implementations of the present disclosure utilize leaf heights for first MLC 302 and second MLC 304 that are the same, or approximately the same. Because both the first MLC 302 and second MLC 304 are responsible for shaping radiation beam 106, both first MLC 302 and second MLC 304 are each preferably designed with leaf heights sufficient to fully attenuate the radiation beam 106, as an example, for medical radiation therapy. In one particular implementation, the leaves of both first MLC 302 and second MLC 304 are made with a tungsten alloy of 17.5 gm/cc or higher density (e.g., 5:5:90 Cu:Ni:W) and are each approximately 5.5 cm thick. A preferred exemplary collimating system may include 34 leaves in each bank of the first MLC 302, and 35 leaves in each bank of the second MLC 304, although different resolutions and numbers of leaves in each bank are contemplated.

It is preferable that the MLCs used with the technology of the present disclosure be double focused, as shown in the drawings (as opposed to using non-focused collimators such as those having linear leaf motion and rounded leaf ends). MLCs are double focused when all of the beam defining surfaces of the leaves project back to the radiation source. For example, with reference to FIG. 1, radiation beam 106 fans out from radiation source 104. Because the exemplary collimating systems utilize curved leaves that retract along an arc (e.g., as shown in FIGS. 1, 3), the edges of the leaves, as they retract, always represent a line projecting back to radiation source 104. With such a design, the entire thickness of the leaves will attenuate beam 106 as it passes through the collimating device, providing for a sharper beam edge with low penumbra regardless of how far the leaves are retracted.

Figure 6:
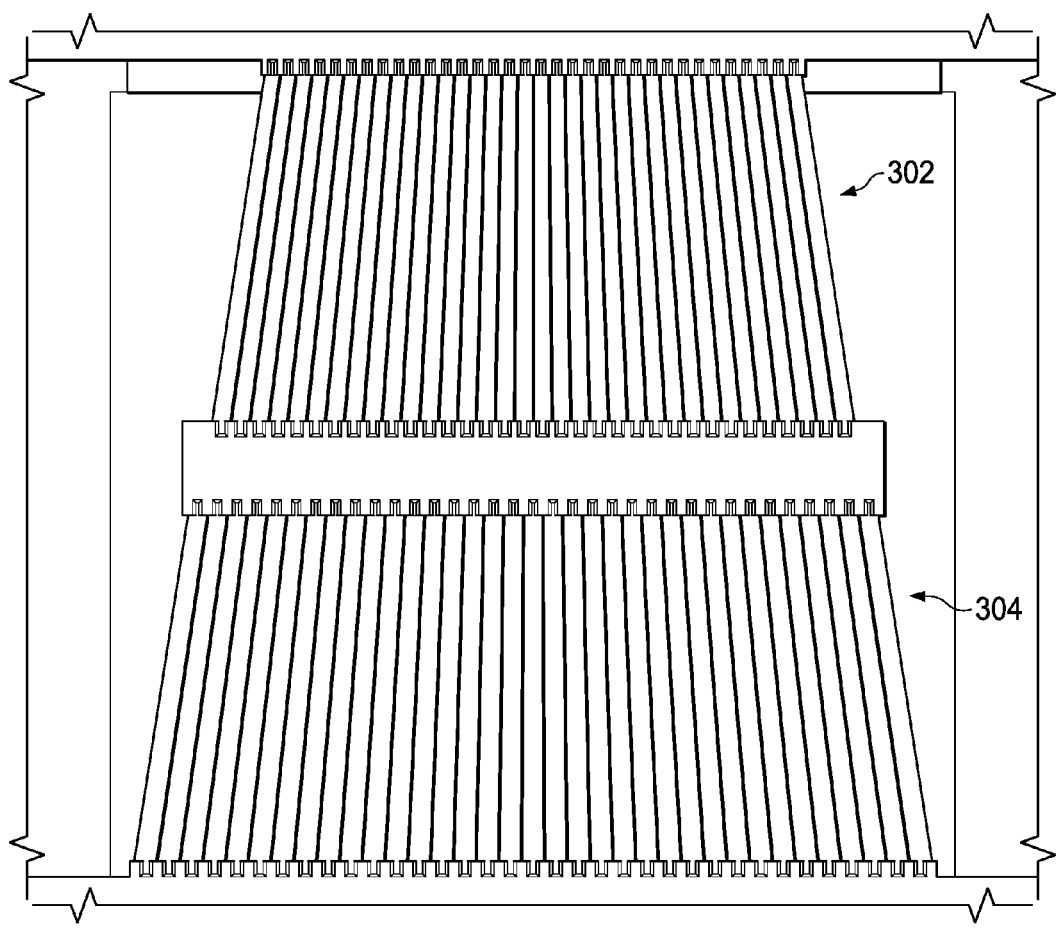
FIG. 6 is a simplified illustration of an exemplary double-stacked collimating device in accordance with certain aspects of the present disclosure.

When all four of the leaf surfaces that collimate beam 106 project back to the radiation source, the collimating system is "double" focused. FIG. 5 illustrates a manner by which the MLCs may focus beam 106 in the other dimension—by virtue of the leaves' width increasing with distance from radiation source 104. In FIG. 5, for example, the width of the leaves at the top of MLC 302 is the thinnest. The width is larger at the bottom of the leaves of MLC 302, larger still at the top of the leaves in second MLC 304, and largest at the bottom of the leaves in MLC 304. This design is also illustrated in FIG. 6.

In one implementation, the focusing of the leaf designs is purposefully defocused slightly. For example, the leaf surfaces may designed to project to a point one to two centimeters above or below the actual radiation source. This slight defocusing can significantly decrease radiation leakage through the space between the leaves (i.e., interleaf gaps), while having only a small impact on beam penumbra.

In another implementation, first MLC 302 and second MLC 304 have different focus points. The arcs on which the MLCs travel would therefore intersect at some point but within their boundaries they can be designed to have sufficient clearance from one another. The differing focus points may be chosen to improve the match of penumbra between the first multileaf collimator and the second multileaf collimator even though they are at different distances from the source. For example, the focus of the first MLC can be placed at the effective source point and the focus of the second MLC can be moved off of the effective source point. Such an exemplary design would increase the penumbra of the lower MLC to better match the penumbra of the upper MLC and provide better dosimetric matching of the beam edges shaped by first MLC and second MLC.

With conventional, non-focused MLCs, collimator jaws are necessary to prevent radiation leakage outside of beam apertures. As the rounded leaf ends of a conventional MLC are poor at blocking radiation even when completely closed, closed leaf ends are often moved to a position where they are blocked by the conventional collimator jaws. The utilization of double focused leaves limits leaf end leakage and penumbra to an extent that an adjacent, stacked MLC of reasonable thickness (having an offset leaf-meeting location) will be sufficient to block transmission so that conventional collimator jaws are not necessary. The present disclosure thus contemplates collimating systems that do not include collimator jaws.

While preferred implementations of the present disclosure utilize double focused MLCs, it is contemplated that single focused or unfocused MLCs may also be utilized, or a mixture of focusing types may be used across multiple stacked MLCs.

When comparing the width of the leaves of first MLC 302 and second MLC 304 in a focused implementation, it is noted above that the leaf width continually increases with distance from radiation source 104. That being said, a preferred implementation of the present disclosure includes leaf designs with approximately the same width in the first MLC 302 as in the second MLC 304. When described in this way, "approximately the same width" means that the bottom width of the leaves in first MLC 302 is approximately the same (i.e., just slightly smaller) than the top width of the leaves in second MLC 304. Stated another way, focused leaves in the first and second MLCs can be thought of as having approximately the same width—including a small additional width being added along the leaves as they extend further from radiation source 104, as is necessary to provide a focused design (e.g., as shown in FIGS. 5 and 6).

While a preferred implementation utilizes leaf designs where leaf widths in first MLC 302 and second MLC 304 are approximately the same, the present disclosure contemplate designs where the leaf widths can be different between the stacked MLCs.

In a preferred implementation of the present disclosure, the leaves of first MLC 302 are immediately adjacent to each other or touching, and the leaves of second MLC 304 are immediately adjacent to one another or touching. In this implementation, the gaps between adjacent leaves in both first MLC 302 and second MLC 304 are minimized in a manner that will minimize radiation leakage between the leaves, yet still allow for relative motion. This type of implementation is illustrated in, for example, FIGS. 4, 5, and 6.

Because the leaves of an MLC are able to move independently, there is necessarily a small gap between them through which some radiation may pass. The collimating system of the present disclosure contemplates that the leaves of first MLC 302 and the leaves of second MLC 304 are preferably arranged so the gaps between leaves are not aligned so radiation beam 106 may not transmit through a leaf gap in first MLC 302 and then directly through a leaf gap in second MLC 304. Instead, the leaves of first MLC 302 are preferably offset from the leaves of second MLC 304 so that there is no straight-line path for the beam to travel through the inter-leaf gaps of both of MLCs. See, for example, FIGS. 4, 5 and 6.

In an exemplary embodiment, the leaves of first MLC 302 and second MLC 304 are offset by approximately 50% of their width so as to provide the greatest separation between the inter-leaf gaps of the first MLC 302 and the second MLC 304. Offsets of less than 50% of the leaf width are contemplated by the present disclosure but an offset is preferably utilized and is preferably is greater than 10% of the width of the leaves.

In typical collimating systems with only one MLC, inter-leaf leakage must be prevented through complex machining of the leaves in the location where they mate or abut one another. For example, tongue and groove or stepped designs may be employed to interrupt an otherwise linear inter-leaf gap that could allow significant beam leakage. The collimating system of the present disclosure contemplates the ability to eliminate such additional machining because, even if straight-edged leaves are utilized, the leakage path through the collimating system will be in interrupted by virtue of the previously described overlap or offset of the leaves between first MLC 302 and second MLC 304. A preferred implementation includes simple, straight-edged leaves without additional machining or features to block interleaf leakage. Such a design may also result in a more uniform leaf edge and decreased beam penumbra.

Figure 7:
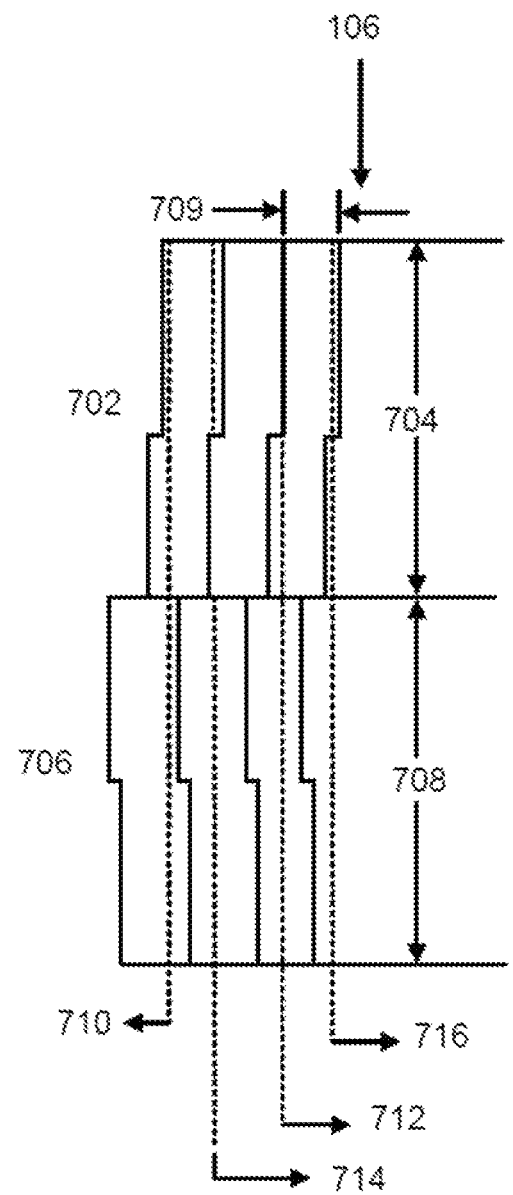
FIG. 7 is a simplified illustration of an exemplary double-stacked collimating device utilizing stepped leaf designs.

In an alternative embodiment of the presently described collimating system, despite having multiple MLCs and leaf offsets, the mating surfaces of the leaves may be machined to further decrease the leakage paths and enable reduction of the height of the MLCs. Any configuration of nonlinear surfaces may prove beneficial, such as a tongue and groove design, or the like. In an exemplary embodiment, depicted in FIG. 7, steps are machined into the mating surfaces of the leaves. FIG. 7 shows a first partial leaf bank 702, corresponding to first MLC 302 and second partial leaf bank 706, corresponding to second MLC 304. In the depicted embodiment, the leaves have a width 709 and heights 704 and 708. In an exemplary embodiment, leaf height 704 of partial leaf bank 702 and leaf height 708 of partial leaf bank 706 are the same and are approximately 5.5 cm. It is not necessary, however, for the height of each of the leaf banks to be the same.

The exemplary leaf mating surface machining depicted in FIG. 7 is a step feature, included in the leaves of both the first MLC 302 and second MLC 304. For the purposes of simplified discussion we will assume that height 704 and height 708 are the same, and both equal to the variable "H". In the example of FIG. 7, there will exist transmission paths such as path 710, where the incident radiation beam 106 must travel through the full height 704 of leaf bank 702, and the full height 708 of leaf bank 706, exhibiting maximum beam attenuation through a thickness of 2×H. However, there are also transmission paths that will encounter inter-leaf gaps, such as paths 712 and 714, which will exhibit decreased attenuation as a result of only passing through a total leaf thickness of H+½ H=3/2 H. Nevertheless, this attenuation thickness of 3/2 H is greater than the thickness of only 1 H that would be encountered in a double stacked collimating system without the "step" feature. The step feature thus allows for a 33% reduction in the total height of the leaves in MLC 302 and MLC 304 to achieve the same attenuation observed by MLCs without the step feature. Such a feature may therefore be used to reduce the amount of material required and the weight of the leaves, thereby improving MLC speed and performance. As an example, the leaf height for each of the MLCs 302 304 may be approximately 3.7 cm.

In a double-stacked design, with offset, the leaf offset will result in beam 106 being attenuated by only about half of the typical amount of material at locations at the edge of aperture 212. Or, if a step feature is utilized, radiation beam 106 will be attenuated by even less material (see, for example, path 716 in FIG. 7).

Figure 8:
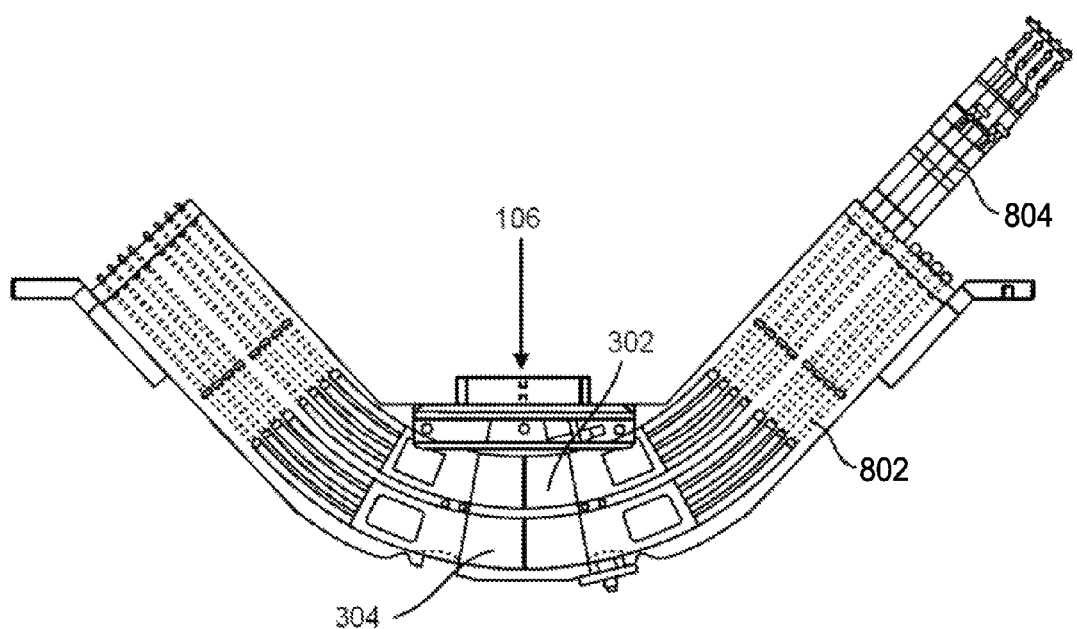
FIG. 8 is a simplified illustration of an exemplary double-stacked collimating device with additional drive hardware in accordance with certain aspects of the present disclosure.

The exemplary MLC assemblies discussed herein may also include mechanical structures for supporting and driving the leaves, servomotors for manipulating the position of the leaves, and control systems for achieving the desired beam shape and attenuation. FIG. 8 is a further depiction of the exemplary collimating system, with the inclusion of drive linkages 802 and leaf drive motor assemblies 804. A number of other related systems such as control systems, encoders, power cables, etc., are not depicted but may also be included.

Figure 9:
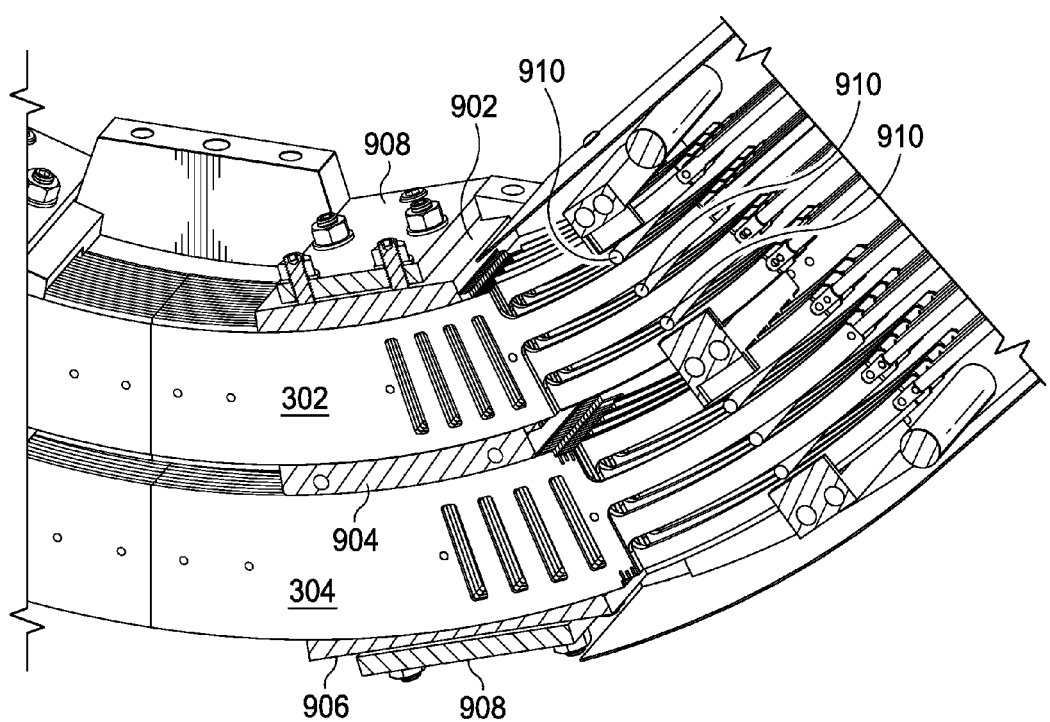
FIG. 9 is a simplified illustration of an exemplary double-stacked collimating device with additional guide hardware accordance with certain aspects of the present disclosure.

FIG. 9 depicts additional structures for supporting and driving the leaves of an exemplary collimating system including a top leaf support guide 902, a middle leaf support guide 904, and a bottom leaf support guide 906. In one embodiment, the leaves include tabs at their top and bottom surfaces, which may ride within grooves in the leaf support guides (see, e.g., FIG. 6). In addition, guide pressure adjustment plates 908 may also be included to ensure smooth, but not loose, movement of the leaves. One particular implementation may also include rods 910 to further guide movement of the leaves and avoid excessive rocking.

Figure 10:
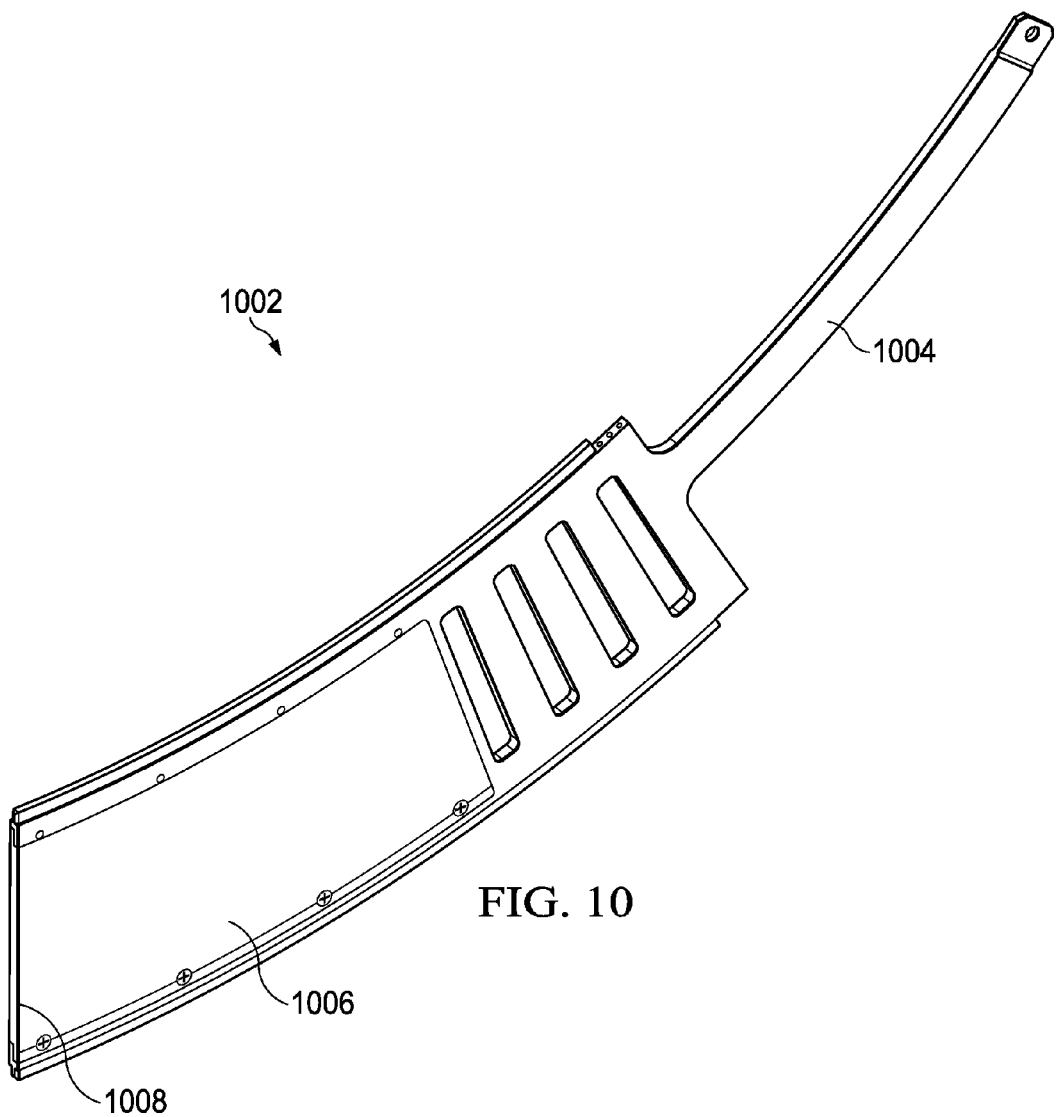
FIG. 10 is a simplified illustration of an exemplary leaf assembly in accordance with certain aspects of the present disclosure.

Referring now to FIG. 10, one implementation for the design of a leaf assembly 1002 utilizes a frame 1004, separate from attenuating material 1006. In such a design, the frame 1004 portion of leaf assembly 1002 that will engage with leaf support guides can be made with a material different from that of attenuating material 1006. While the attenuating material 1006 is typically a tungsten alloy or other high density material for radiation attenuation, the frame 1004 may be made from another material, for example, stainless steel. Attenuating material 1006 may be designed to be an insert into frame 1004 and the two materials may be fixed together using a number of methods such as bonding, sintering or welding. Preferably, frame 1004 does not extend all the way to the attenuating edge 1008 of leaf assembly 1002 to avoid variation in the overall attenuating properties of the leaf assembly 1002.

One or more aspects or features of the subject matter described herein, for example, the control systems for multileaf collimators, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Aspects of the subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A collimating system for collimating a radiation beam from a radiation source, the beam being directed at a target, comprising:
    a first multileaf collimator having a plurality of leaves;
    a second multileaf collimator having a plurality of leaves and configured such that the radiation beam will pass through the first multileaf collimator before passing through the second multileaf collimator, and pass through the second multileaf collimator before hitting the target;
    wherein the leaves of the first multileaf collimator and the leaves of the second multileaf collimator are configured to move independently of one another; and
    wherein at least one of the first multileaf collimator and the second multileaf collimator is double focused.

2. The collimating system of claim 1 wherein the first multileaf collimator and the second multileaf collimator are both double focused.

3. The collimating system of claim 2 wherein the first multileaf collimator and the second multileaf collimator are configured to be slightly defocused to decrease radiation leakage through interleaf gaps.

4. The collimating system of claim 3 wherein the first multileaf collimator and the second multileaf collimator are configured to be defocused by approximately 1 centimeter.

5. The collimating system of claim 2 wherein the first multileaf collimator has a focus point and the second multileaf collimator has a focus point and the focus point of the first multileaf collimator is different from the focus point of the second multileaf collimator.

6. The collimating system of claim 5 wherein the differing focus points of the first multileaf collimator and the second multileaf collimator improve the match of penumbra between the first multileaf collimator and the second multileaf collimator.

7. The collimating system of claim 5 wherein the focus point of the first multileaf collimator is at the effective source point and the focus point of the second multileaf collimator is moved off of the effective source point.

8. The collimating system of claim 1 wherein the first multileaf collimator and second multileaf collimator are further configured to collimate a beam thinner than the widths of the leaves of the first and second multileaf collimators.

9. The collimating system of claim 1 wherein the leaves of the first multileaf collimator have approximately the same width as the leaves of the second multileaf collimator.

10. The collimating system of claim 1 wherein the leaves of the first multileaf collimator are immediately adjacent to one another and the leaves of the second multileaf collimator are immediately adjacent to one another.

11. The collimating system of claim 1 wherein gaps between adjacent leaves in the first multileaf collimator and gaps between adjacent leaves in the second multileaf collimator are minimized to reduce radiation leakage.

12. The collimating system of claim 1 wherein the leaves of both the first multileaf collimator and the second multileaf collimator are approximately 4 mm wide.

13. The collimating system of claim 1 wherein the leaves of the first multileaf collimator and the leaves of the second multileaf collimator are offset by approximately 50% of their width.

14. The collimating system of claim 1 wherein the thickness of the leaves of the first multileaf collimator and the thickness of the leaves of the second multileaf collimator are approximately the same.

15. The collimating system of claim 1 wherein the thickness of the leaves of the first multileaf collimator and the thickness of the leaves of the second multileaf collimator are each sufficient to fully attenuate the radiation beam for medical radiation therapy.

16. The collimating system of claim 15 wherein the thickness of the leaves of both the first multileaf collimator and the second multileaf collimator are approximately 5.5 cm.

17. The collimating system of claim 1 wherein the mating surfaces of the leaves are straight edged.

18. The collimating system of claim 1 wherein the mating surfaces of the leaves are machined to provide a tongue and groove interface.

19. The collimating system of claim 1 wherein the mating surfaces of the leaves are machined to provide a step interface.

20. The collimating system of claim 1 wherein leaves of the first and second multileaf collimators comprise leaf assemblies utilizing a frame separate from an attenuating material.

21. The collimating system of claim 20 wherein the frame is made from a stainless steel alloy and the attenuating material is a tungsten alloy.

22. The collimating system of claim 1 wherein the first multileaf collimator has two banks and each bank includes 34 leaves and wherein the second multileaf collimator has two banks and each bank includes 35 leaves.

23. The collimating system of claim 1 wherein the edge of the collimating system closest to the target is less than 60 cm from a radiation isocenter.

24. The collimating system of claim 1 wherein the system does not include collimator jaws.

* * * * *